(12) United States Patent
Stone et al.

(10) Patent No.: US 8,574,275 B2
(45) Date of Patent: Nov. 5, 2013

(54) FIXATION DEVICE FOR DELIVERY OF BIOLOGIC MATERIAL BETWEEN SOFT TISSUE AND BONE

(75) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 334 days.

(21) Appl. No.: 12/881,829

(22) Filed: Sep. 14, 2010

(65) Prior Publication Data

US 2011/0004258 A1   Jan. 6, 2011

Related U.S. Application Data

(63) Continuation of application No. 11/745,226, filed on May 7, 2007, now Pat. No. 7,794,484.

(51) Int. Cl.
A61B 17/04 (2006.01)
A61B 17/86 (2006.01)
A61F 2/08 (2006.01)

(52) U.S. Cl.
USPC .......................................................... 606/313

(58) Field of Classification Search
USPC .................................. 606/304–305, 313–314
See application file for complete search history.

(56) References Cited

U.S. PATENT DOCUMENTS

| | | |
|---|---|---|
| 3,708,883 A | 1/1973 | Flander |
| 4,409,974 A | 10/1983 | Freedland |
| 4,653,489 A | 3/1987 | Tronzo |
| 4,738,255 A | 4/1988 | Goble et al. |
| 5,013,316 A | 5/1991 | Goble et al. |
| 5,087,199 A | 2/1992 | Lazarof |
| 5,167,665 A | 12/1992 | McKinney |
| 5,258,016 A | 11/1993 | DiPoto et al. |
| 5,268,001 A | 12/1993 | Nicholson et al. |
| 5,326,205 A | 7/1994 | Anspach, Jr. et al. |
| 5,464,427 A | 11/1995 | Curtis et al. |
| 5,472,452 A | 12/1995 | Trott |
| 5,474,572 A | 12/1995 | Hayhurst |
| 5,480,403 A | 1/1996 | Lee et al. |
| 5,486,197 A | 1/1996 | Le et al. |
| 5,501,695 A | 3/1996 | Anspach, Jr. et al. |
| 5,531,792 A | 7/1996 | Huene |
| 5,584,835 A | 12/1996 | Greenfield |
| 5,601,558 A | 2/1997 | Torrie et al. |
| 5,643,321 A | 7/1997 | McDevitt |
| 5,645,589 A | 7/1997 | Li |
| 5,649,963 A | 7/1997 | McDevitt |
| 5,665,110 A | 9/1997 | Chervitz et al. |
| 5,713,903 A | 2/1998 | Sander et al. |

(Continued)

OTHER PUBLICATIONS

Cannulated ArthroRivet™ Anchor brochure, Arthrotek® Aug. 2003.

(Continued)

*Primary Examiner* — Sameh Boles
(74) *Attorney, Agent, or Firm* — Harness, Dickey

(57) ABSTRACT

A fixation device for delivery of biological material between soft tissue and bone. The fixation device includes an anchor having a first longitudinal bore and a first radial extending delivery bore and an insert having a second longitudinal bore and a second radial extending delivery bore. The first and second radial extending bores are aligned and positioned relative to a head of the anchor to deliver the biologic material between the soft tissue and the bone.

24 Claims, 10 Drawing Sheets

(56) References Cited

U.S. PATENT DOCUMENTS

| | | | |
|---|---|---|---|
| 5,720,753 A | 2/1998 | Sander et al. | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,814,071 A | 9/1998 | McDevitt et al. | |
| 5,911,721 A | 6/1999 | Nicholson et al. | |
| 5,928,244 A * | 7/1999 | Tovey et al. | 606/104 |
| 5,931,844 A | 8/1999 | Thompson et al. | |
| 5,935,129 A | 8/1999 | McDevitt et al. | |
| 5,941,901 A | 8/1999 | Egan | |
| 5,968,044 A | 10/1999 | Nicholson et al. | |
| 6,048,343 A | 4/2000 | Mathis et al. | |
| 6,056,751 A | 5/2000 | Fenton, Jr. | |
| 6,129,762 A | 10/2000 | Li | |
| 6,149,669 A | 11/2000 | Li | |
| 6,210,376 B1 | 4/2001 | Grayson | |
| 6,214,012 B1 * | 4/2001 | Karpman et al. | 606/93 |
| 6,227,860 B1 | 5/2001 | Hobo et al. | |
| 6,315,787 B1 | 11/2001 | Tsugita et al. | |
| 6,319,269 B1 | 11/2001 | Li | |
| 6,328,758 B1 | 12/2001 | Tornier et al. | |
| 6,447,516 B1 | 9/2002 | Bonutti | |
| 6,464,706 B1 | 10/2002 | Winters | |
| 6,517,564 B1 | 2/2003 | Grafton et al. | |
| 6,524,316 B1 | 2/2003 | Nicholson et al. | |
| 6,527,794 B1 | 3/2003 | McDevitt et al. | |
| 6,554,830 B1 | 4/2003 | Chappius | |
| 6,565,572 B2 * | 5/2003 | Chappius | 600/300 |
| 6,575,976 B2 | 6/2003 | Grafton | |
| 6,582,453 B1 | 6/2003 | Tran et al. | |
| 6,599,295 B1 | 7/2003 | Tornier et al. | |
| 6,623,492 B1 | 9/2003 | Berube et al. | |
| 6,641,596 B1 | 11/2003 | Lizardi | |
| 6,645,227 B2 | 11/2003 | Fallin et al. | |
| 6,652,561 B1 | 11/2003 | Tran | |
| 6,660,023 B2 | 12/2003 | McDevitt et al. | |
| 6,770,073 B2 | 8/2004 | McDevitt et al. | |
| 6,863,671 B1 | 3/2005 | Strobel et al. | |
| 6,994,725 B1 | 2/2006 | Goble | |
| 7,037,324 B2 | 5/2006 | Martinek | |
| 7,250,055 B1 | 7/2007 | Vanderwalle | |
| 7,572,283 B1 * | 8/2009 | Meridew | 606/321 |
| 2001/0051807 A1 | 12/2001 | Grafton | |
| 2002/0095180 A1 | 7/2002 | West et al. | |
| 2002/0111653 A1 | 8/2002 | Foerster | |
| 2002/0128684 A1 | 9/2002 | Foerster | |
| 2003/0144667 A1 | 7/2003 | Enayati | |
| 2003/0181986 A1 * | 9/2003 | Buchholz | 623/22.12 |
| 2003/0187444 A1 | 10/2003 | Overaker et al. | |
| 2004/0133239 A1 | 7/2004 | Singhatat | |
| 2004/0138707 A1 | 7/2004 | Greenhalgh | |
| 2004/0193167 A1 | 9/2004 | Tucciarone et al. | |
| 2004/0225292 A1 | 11/2004 | Sasso et al. | |
| 2004/0243179 A1 | 12/2004 | Foerster | |
| 2004/0267265 A1 | 12/2004 | Kyle | |
| 2005/0015059 A1 | 1/2005 | Sweeney | |
| 2005/0075668 A1 | 4/2005 | Lizardi | |
| 2005/0137707 A1 | 6/2005 | Malek | |
| 2006/0235413 A1 | 10/2006 | Denham et al. | |
| 2007/0112352 A1 | 5/2007 | Sorensen et al. | |
| 2007/0265704 A1 | 11/2007 | Mayer et al. | |
| 2008/0281325 A1 | 11/2008 | Stone et al. | |
| 2009/0299386 A1 | 12/2009 | Meridew | |

OTHER PUBLICATIONS

Cannulated ArthroRivet™, Arthrotek® Inventing the Future of Arthroscopy, print out of web site http://www.arthrotek.com/prodpage.cfm?c=0A05&p=0102 (printed Dec. 12, 2006) Copyright 2005, Arthrotek, Inc.

* cited by examiner

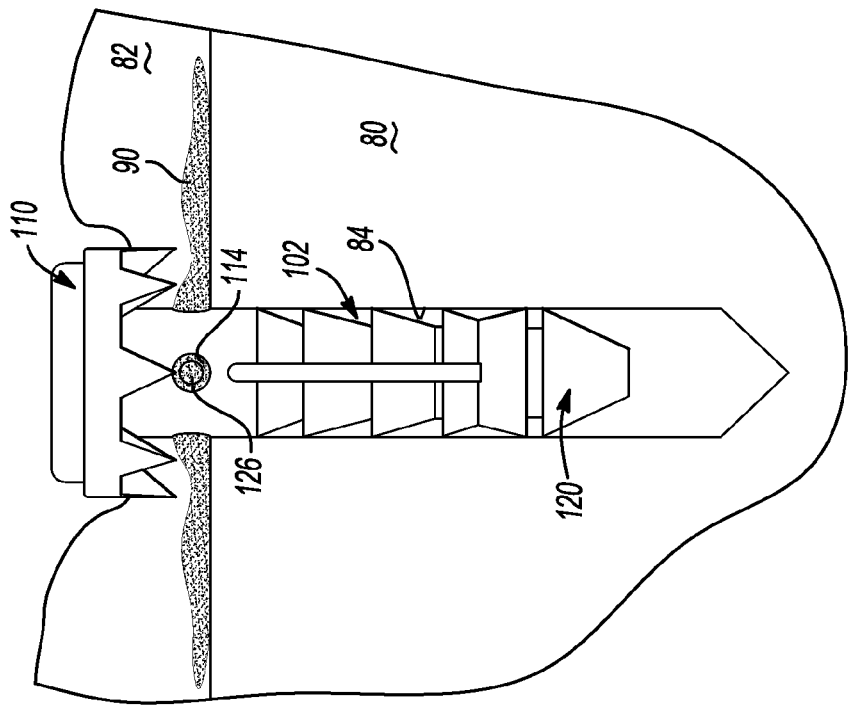
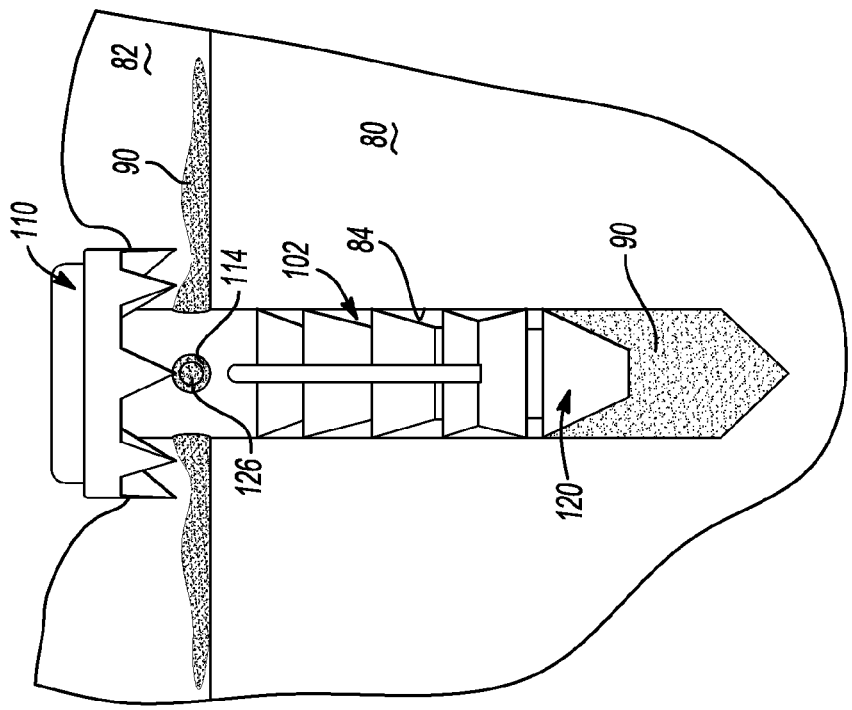

FIXATION DEVICE FOR DELIVERY OF BIOLOGIC MATERIAL BETWEEN SOFT TISSUE AND BONE

CROSS-REFERENCE TO RELATED APPLICATIONS

This application is a continuation of U.S. patent application Ser. No. 11/745,226 filed on May 7, 2007. The entire disclosure of the above application is incorporated herein by reference.

INTRODUCTION

Various methods and devices for attaching soft tissue to a bone are known. Some methods use various suture anchors or expandable suture anchors, or rivets for knotless tying.

The present teachings provide fixation devices adapted for arthroscopic delivery of biologic material.

SUMMARY

The present teachings provide a fixation device deployable for attaching soft tissue to a bone. The fixation device includes a cannulated anchor and a cannulated insert engageable with the anchor. The anchor includes a soft-tissue engaging portion and a bone-anchoring portion. The bone-anchoring portion includes an expandable body having a proximal end and a distal end. The proximal end defines at least one radial delivery hole adjacent the soft-tissue engaging portion. The insert has a proximal end and a distal end and defines at least one radial delivery hole at the proximal end of the insert. The delivery holes of the anchor and insert are aligned and positioned such that biologic material can be delivered through the delivery holes and flow between the tissue and the bone when the fixation device is deployed.

The present teachings further provide a fixation device that includes an anchor and an insert engageable with the anchor and received in bone. The anchor and insert are movable between a non-deployed and a deployed position. The anchor has a first portion engaging soft tissue and an expandable second portion adjacent the first portion and received in bone below the soft tissue. The first portion has first and second ends, and the second portion has first and second ends. The second end of first portion is adjacent the first end of the second portion. The fixation device defines a plurality of radial delivery holes adjacent the first end of the second portion at an area between the soft tissue and the bone when the fixation device is in the deployed position, such that biologic material can be delivered through the delivery holes between the soft tissue and the bone.

The present teachings provide a fixation device deployable for attaching soft tissue to a bone and including a cannulated anchor and a cannulated insert. The anchor has a head engageable with the soft tissue and an expandable body receivable in the bone and defining at least one radial delivery hole at a proximal portion of the anchor under the head. The insert is movable relative to the anchor for expanding the expandable member. The insert defines at least one radial delivery hole. The delivery holes of the anchor and insert are aligned such that biologic material can be delivered through the delivery holes and flow between the tissue and the bone when the fixation device is deployed.

The present teachings provide an apparatus for attaching soft tissue to a bone and including a suture anchor having a first portion engageable with a suture and a second portion engageable with bone, and a cannulated shaft having a longitudinal bore, the shaft engageable with the first portion of the suture anchor. The shaft has at least one radial delivery aperture communicating with the longitudinal bore, the aperture located along the shaft at a position capable for delivering biologic material between the soft tissue and the bone when the shaft is engaged with the first portion of the anchor.

The present teachings provide a fixation device deployable for attaching soft tissue to a bone. The fixation device includes an anchor having a soft-tissue engaging portion and a bone-anchoring portion. The bone-anchoring portion includes a body having a proximal end and a distal end, the proximal end of the bone anchoring portion defining at least one radial delivery aperture defined adjacent the soft-tissue engaging portion and adapted for delivering biologic material through the anchor and between the soft tissue and the bone.

The present teachings also provide methods for attaching soft tissue to bone. In one aspect, the method includes forming a bore in a bone, placing the soft tissue adjacent to the bone and above the bore, at least partially inserting a fixation device into the bore, and delivering biologic material through the soft tissue at an interface area between the soft tissue and the bone.

In another aspect, the method includes forming a bore in a bone, placing a soft tissue adjacent to the bone and above the bore, holding the soft tissue against the bone with an enlarged head of a fixation device, inserting a bone-anchoring portion of the fixation device into the bore, and delivering biologic material through the soft tissue at an interface area between the soft tissue and the bone.

In another aspect, the method includes inserting a fixation device through the soft tissue into the bone, anchoring the soft tissue to the bone with the fixation device, and delivering biologic material at an interface area between the soft tissue and the bone.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A is a side view of the fixation device of FIG. 2;

FIG. 11 is an environmental view of a fixation device according to the present teachings showing delivery of biologic material through the fixation device;

FIG. 11A is an environmental view of a fixation device according to the present teachings showing delivery of biologic material through the fixation device;

DESCRIPTION OF VARIOUS ASPECTS

Figure 13:
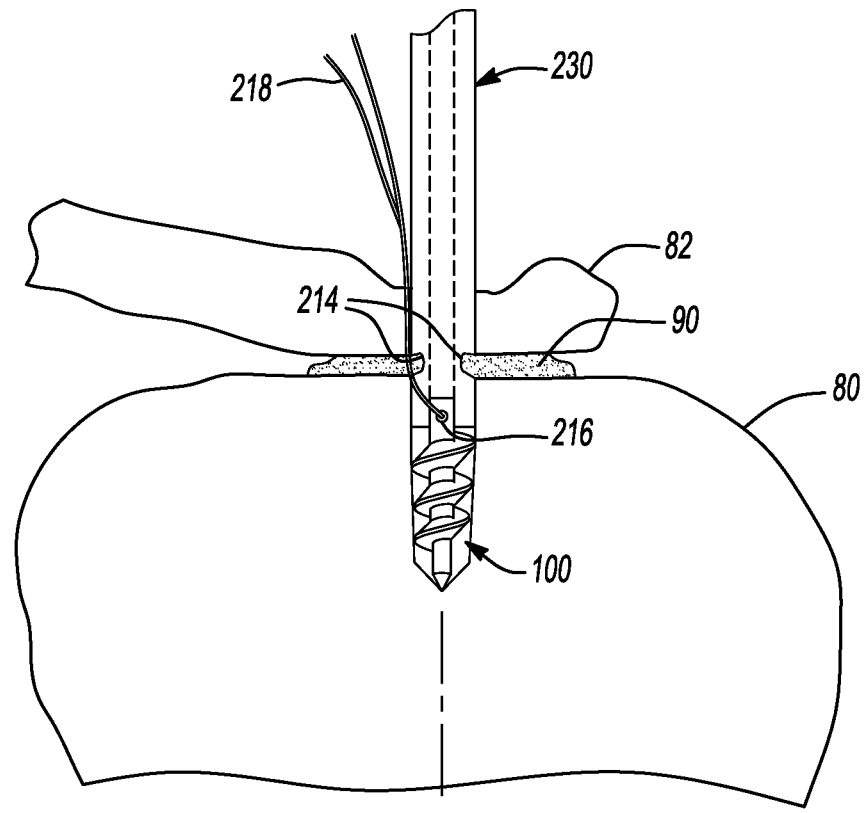
FIG. 13 is an environmental view of a fixation device according to the present teachings showing delivery of biologic material through the fixation device.

The following description is merely exemplary in nature and is in no way intended to limit the invention, its application, or uses. For example, although the present teachings are illustrated in connection particular fixation devices used in arthroscopic surgery, the present teachings can be applied to other fixation devices. The present teachings can be applied, for example, to expandable fixation devices, such as the fixation device illustrated in FIG. 1, or the fixation devices disclosed in co-pending patent applications Ser. No. 11/006418, filed Dec. 7, 2004, ("Ref. A"), now U.S. Pat. No. 7,572,283, Ser. No. 11/006398 filed Dec. 7, 2004 ("Ref. B"), and Ser. No. 11/451250 filed Jun. 12, 2006 ("Ref. C"), now published as U.S. 2006-0235413. The disclosures of these applications are incorporated herein by reference. Further, the present teachings can be applied to non-expandable fixation devices, such as, for example, suture anchors, as illustrated in FIG. 13, or other fixation devices.

Generally, the fixation devices can include any type of soft tissue fixation device, including for example, tacks, or suture anchors or expandable or deployable devices, cannulated rivets, screws or other anchors. The fixation device 100 can be used with an inserter or other cannulated or tubular shaft to deliver biologic material 90 at the interface between the soft tissue 82 and the bone 80 for various soft tissue repair procedures, as described below. The biologic material 90 can flow at the interface of the soft tissue 82 and bone 80 through cannulation and/or other apertures of the fixation device 100, as described below in connection with FIGS. 1-12, and/or through apertures of an inserter shaft that can be used to insert the fixation device and/or deliver the biologic material, as described in connection with FIGS. 13-13B.

It will be appreciated that depending on the particular fixation and delivery/inserter devices, the biologic material can be delivered after the fixation device is fully deployed or fully seated, or while the fixation device is partially seated or partially deployed. In other applications, deploying or seating the fixation device can cause delivery of the biologic material, or conversely, delivering the biologic material can cause seating or deployment of the fixation device.

Figure 1:
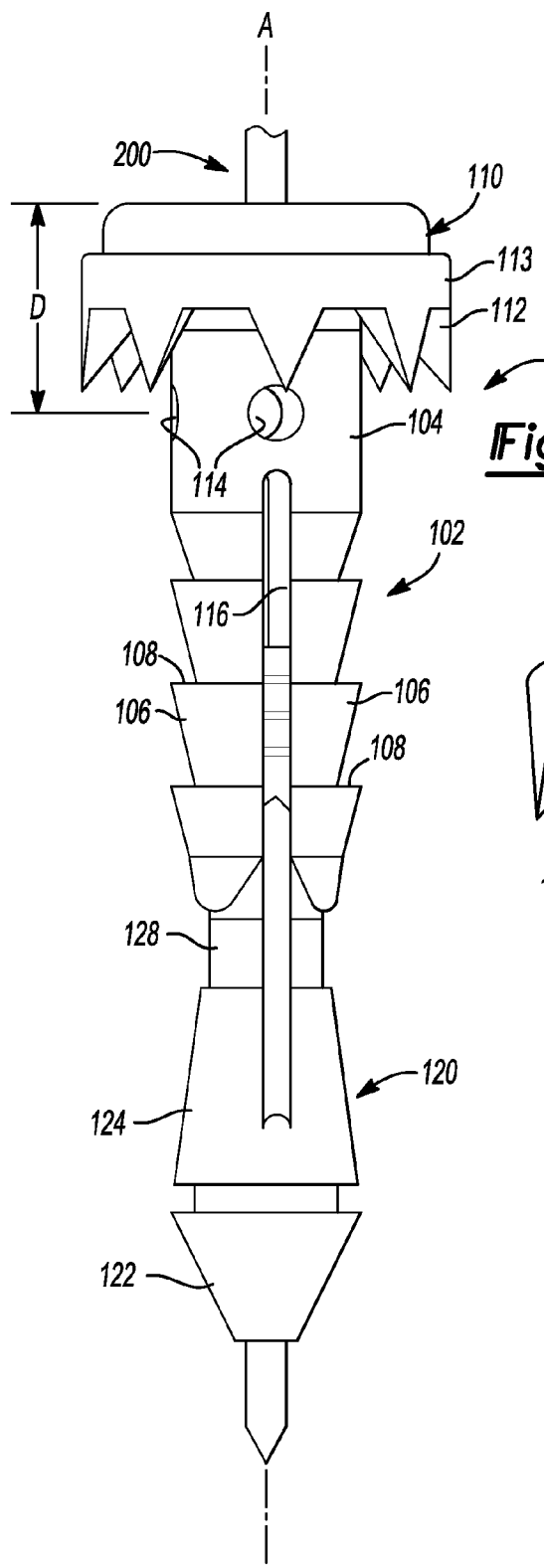
FIG. 1 is a side view of a fixation device according to the present teachings, shown with a guide pin.
Figure 2:
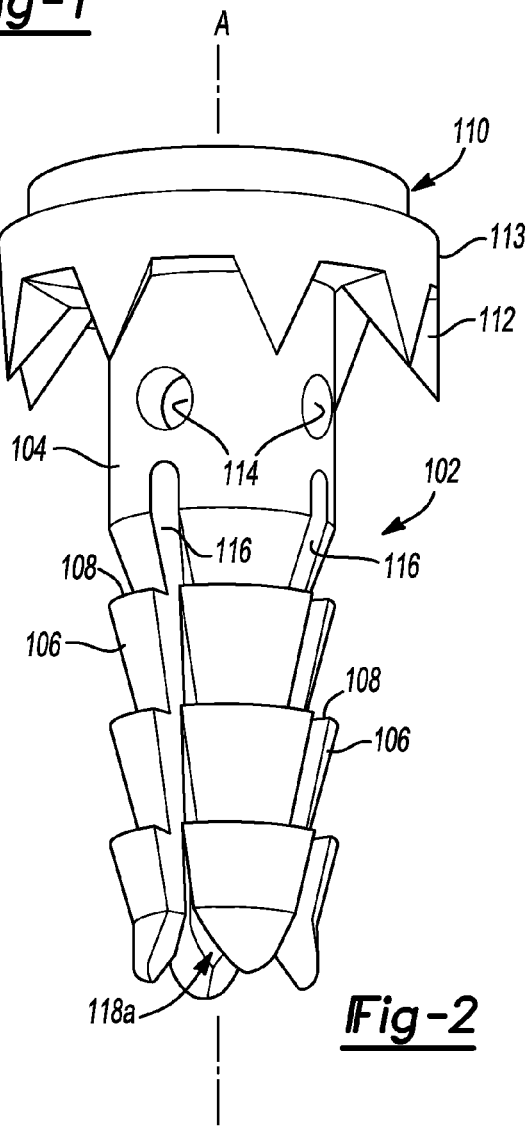
FIG. 2 is a perspective view of an expandable member of the fixation device of FIG. 1.
Figure 3:
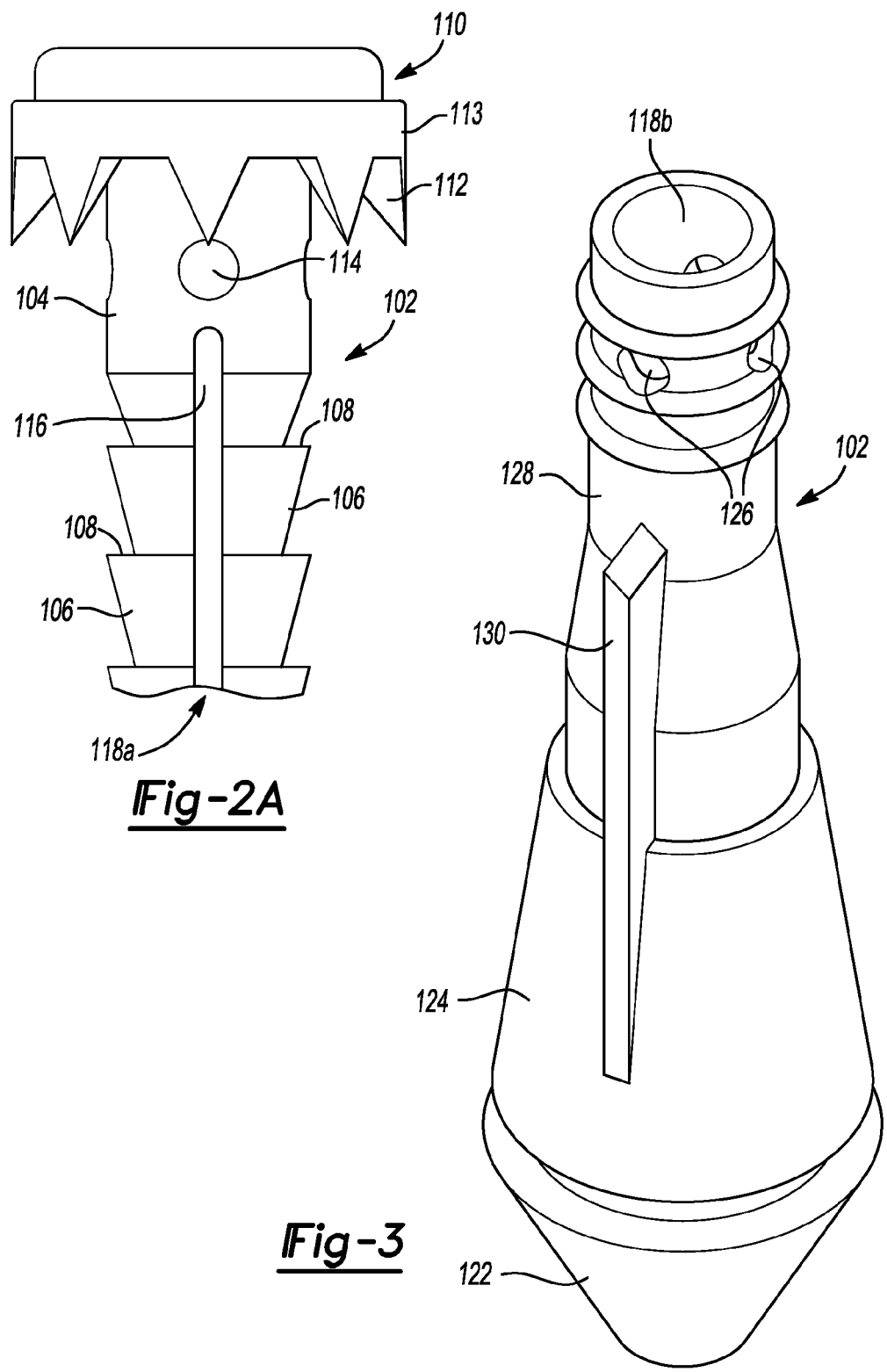
FIG. 3 is a perspective view of an insert of the fixation device of FIG. 1
Figure 4:
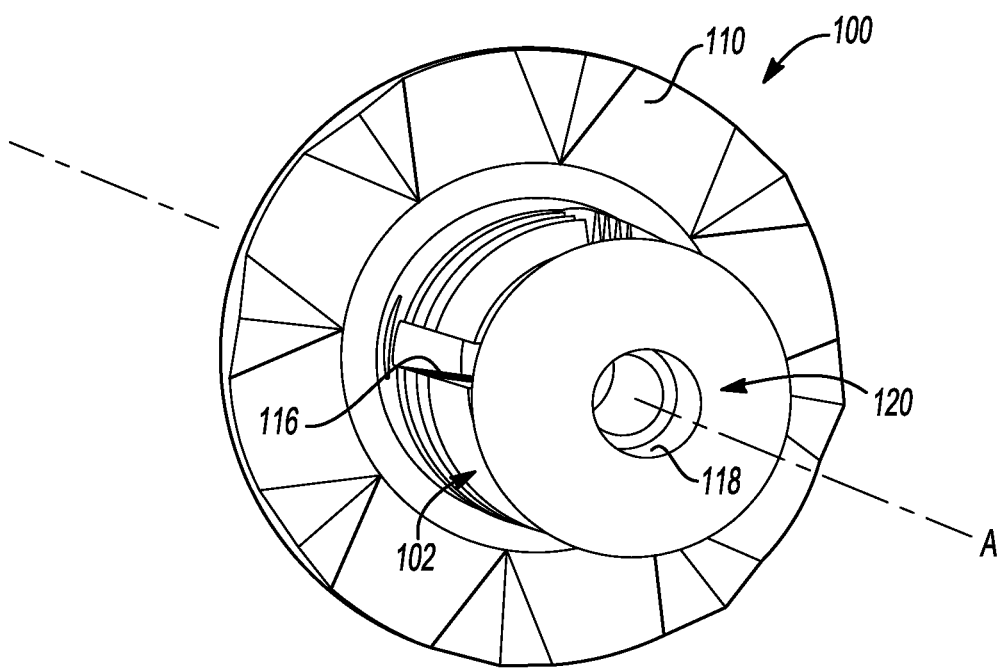
FIG. 4 is a bottom perspective view of the fixation device of FIG. 1.

Referring to FIGS. 1-12, the present teachings provide an expandable fixation device 100, shown in FIG. 1 that can be arthroscopically implanted through soft tissue into bone. The fixation device 100 can be made of a resorbable material, such a resorbable copolymer, Lactosorb© or other biocompatible material. The fixation device 100 can be implanted into a prepared hole in the bone, for example, and used to reattach damaged soft tissue. The fixation device 100 can be used in various arthroscopic procedures, including, but not limited to, various shoulder repair procedures, such as, bankart procedures, SLAP lesion repairs, acromioclavicular separation repairs, capsular shift or capsulolabral reconstructions, biceps tenodesis, deltoid repairs, rotator cuff repairs, and others. The fixation device 100 can provide strong tissue fixation while eliminating knot tying and suture management problems.

The fixation device 100 can include various structural features that allow the delivery of biologic materials at the fixation site, as described below. The biologic materials can be selected, for example, for promoting the healing of soft tissue and/or bone during arthroscopic surgery, for improving and/or increasing the rate of fixation, or for other purposes. The biologic materials can include, for example, platelet-rich plasma, growth factors, bone/soft tissue glue, stem cells, pharmaceuticals, nutrients, or other biologic materials.

Referring to FIGS. 1-4, an exemplary fixation device 100 according to the present teachings can include a cannulated anchor 102 having a longitudinal bore 118a, and a cannulated insert 120 having a longitudinal bore 118b. The bores 118a, 118b of the anchor 102 and the insert 120 are coaxial and define a longitudinal bore 118 of the fixation device 100. The anchor 102 includes an expandable body 104. The expandable body 104 can include expanding members 106 defined by longitudinal slots 116. The expanding members 106 can include ridges, barbs, or other bone-anchoring formations 108 that can engage bone when the expandable body 104 is in an expanded configuration, as discussed below. The anchor 102 can also include a washer-like head 110 with a distal portion 113 defining teeth, spikes, barbs, serrations or other anchoring protrusions 112. A guide pin 200 can pass through the longitudinal bore 118 of the fixation device 100 for guiding the insertion of the fixation device 100 and facilitating deployment of the expandable members 106, as discussed below and in more detail in Ref. A.

The insert 120 can be bullet-shaped portion and have distal portion 122 that tapers distally, an intermediate portion 124 that tapers proximally, and a proximal portion 128. The insert 120 can include a pair of opposing and distally tapering flanges 130 that can engage an insertion instrument, as described in Ref. A. The proximal portion 128 can include a grip portion 132 with circumferential protrusions or other grip elements for firmly engaging the insert 120 into the bore 128a of the anchor 102 in the deployed configuration. These and other features of the anchor 102 and insert 120 as well as alternative features can be found in Refs. A-C.

Figure 5:
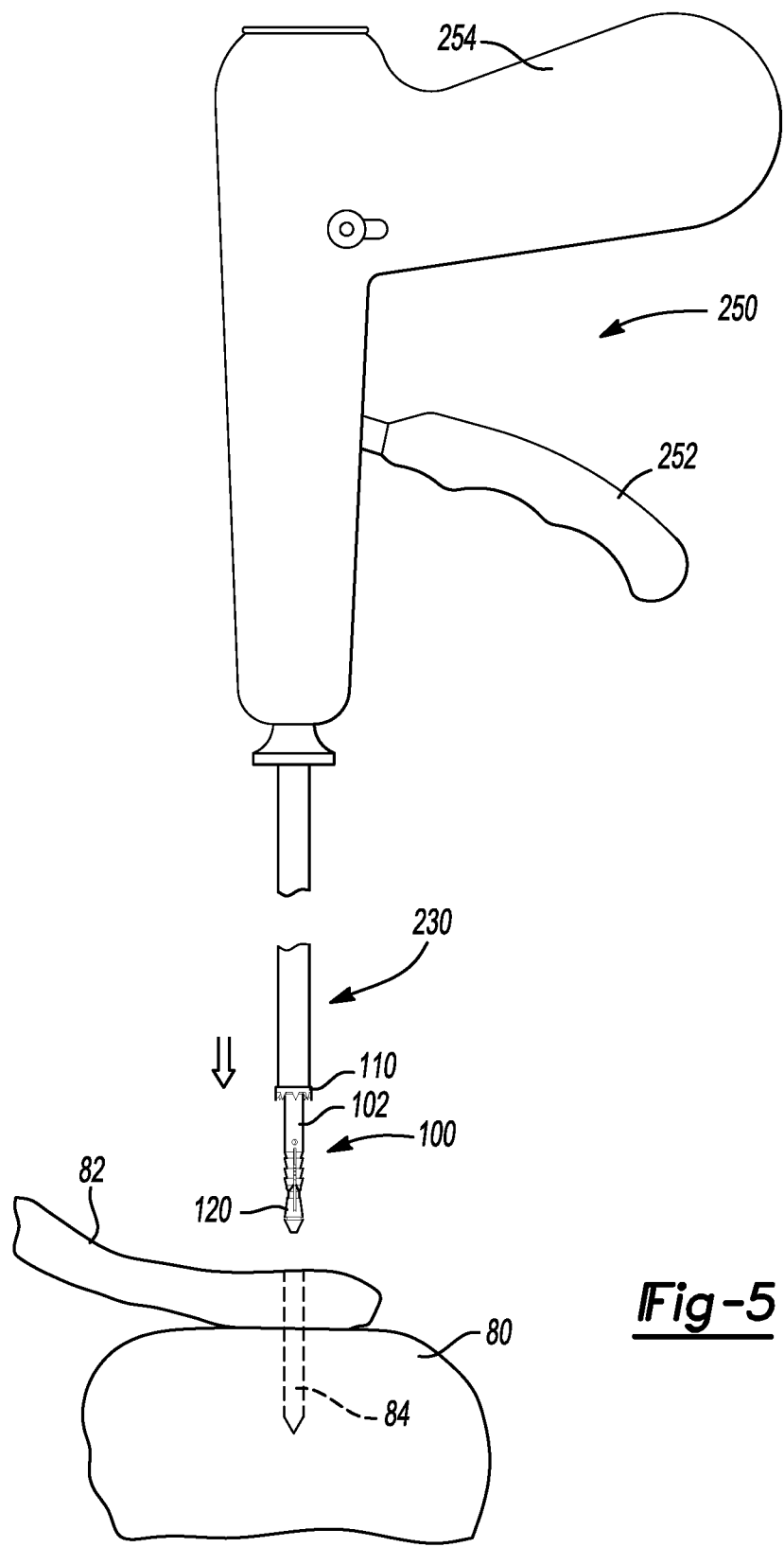
FIG. 5 is an environmental view of the fixation device of FIG. 1, shown with an insertion system.
Figure 6:
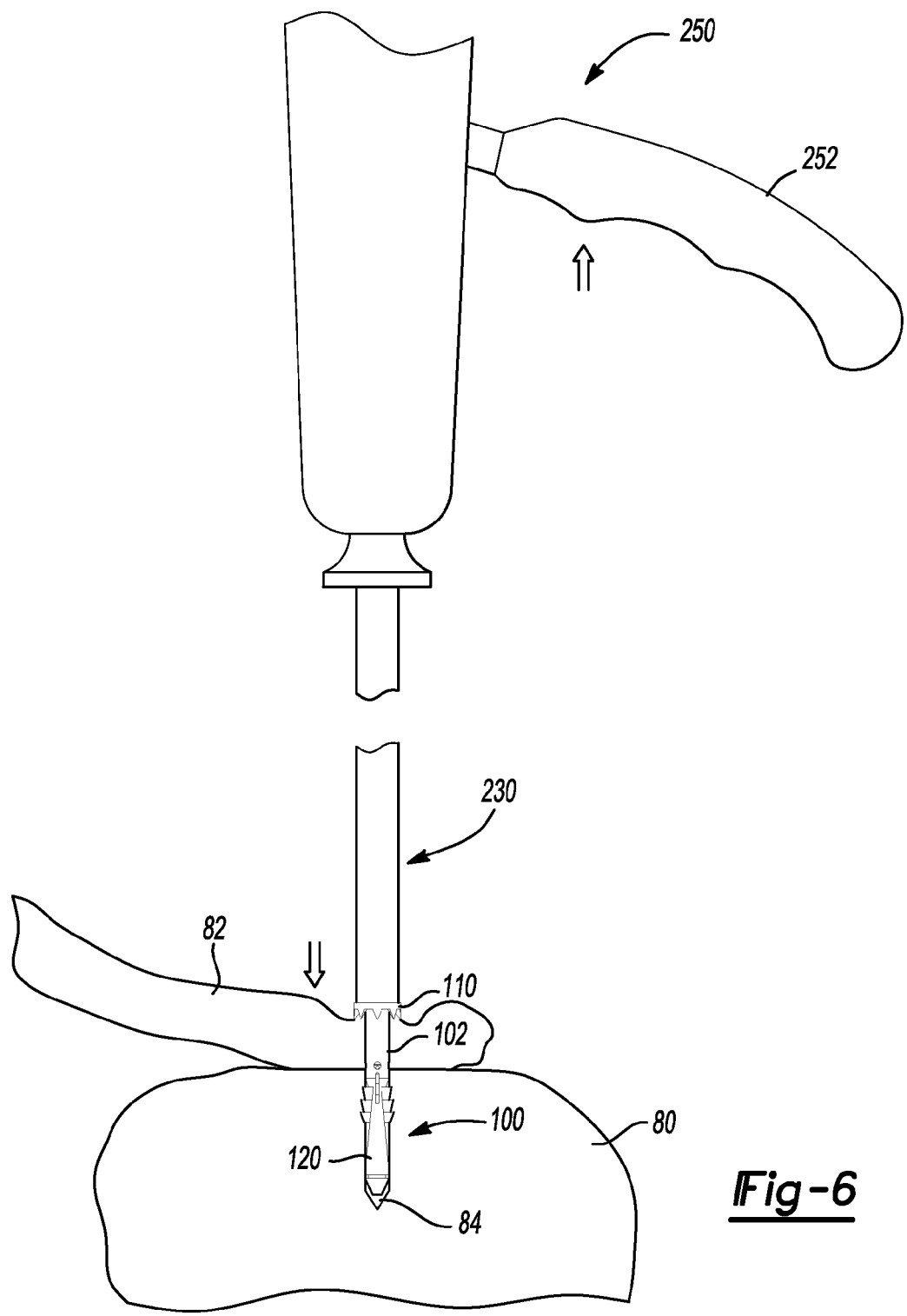
FIG. 6 is an environmental view of the fixation device of FIG. 1, shown seated in bone.
Figure 7:
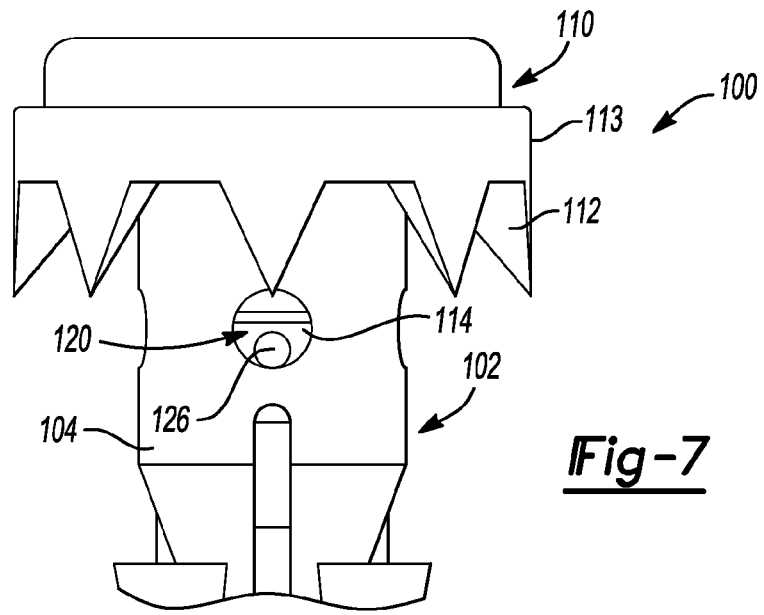
FIG. 7 is an enlarged detail the fixation device of FIG. 1, shown after deployment in bone.
Figure 8:
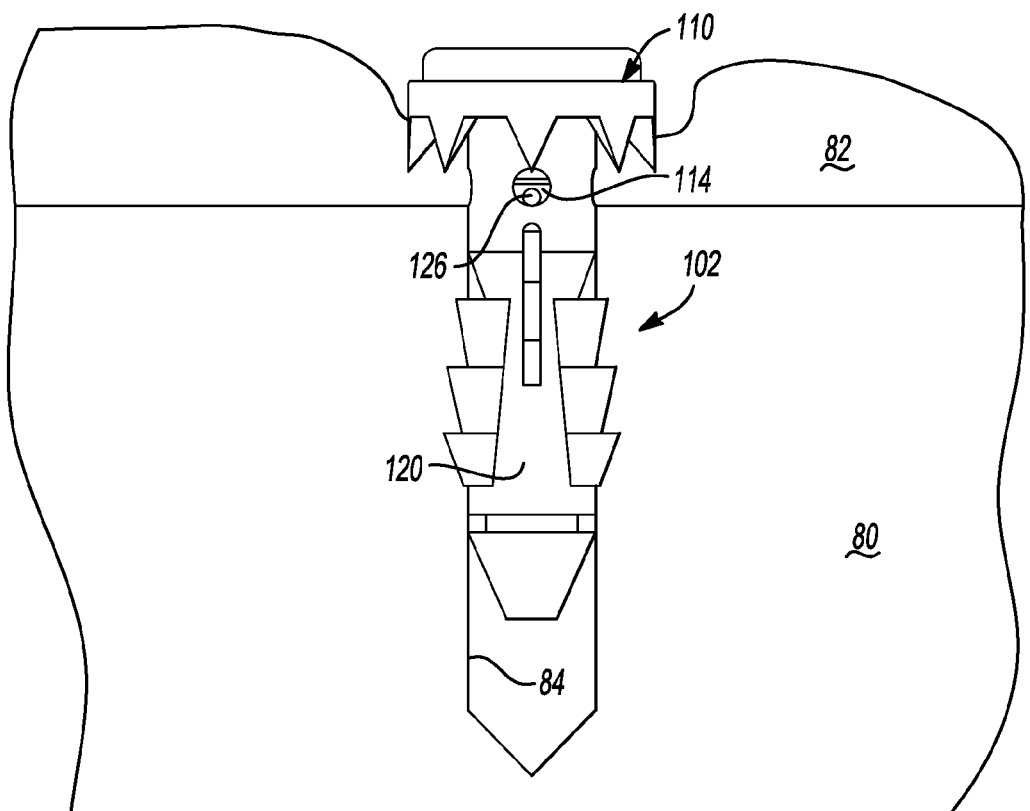
FIG. 8 is an environmental view of the fixation device of FIG. 1, shown after deployment in bone.
Figures 9, 10:
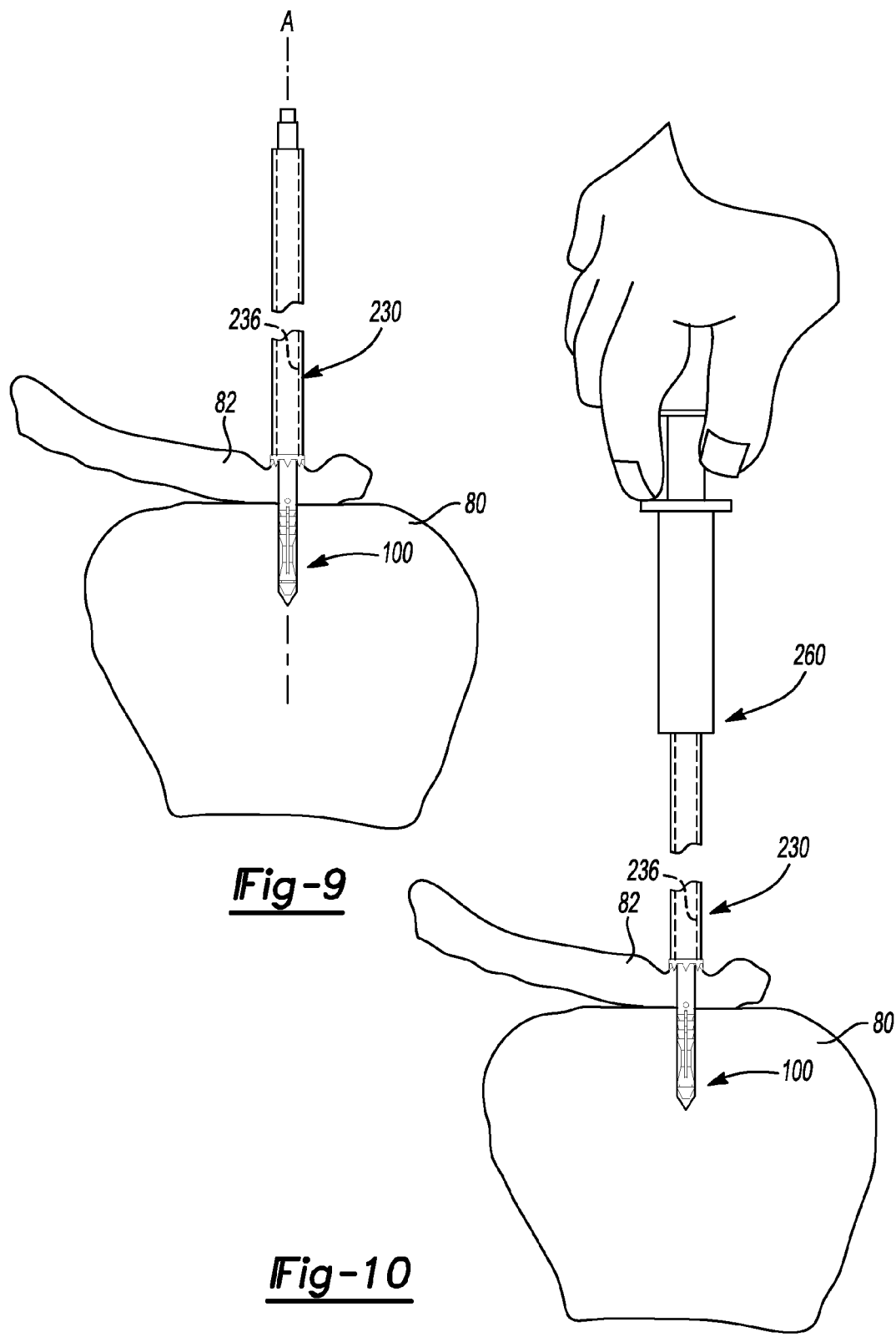
FIGS. 9 and 10 illustrate aspects of delivering biologic material through a fixation device according to the present teachings.

Referring to FIGS. 5 and 6, an exemplary method of using the fixation device 100 to attach soft tissue 82 to a bone 80 is illustrated. A deployment instrument 250 can be used to insert the fixation device 100 to a bone bore 84 drilled in the bone 80. The deployment instrument 250 can be in the form of a gun that includes a handle 250, a tubular shaft 230 having a longitudinal bore 236 and a trigger 252 that can be used for actuating movement of the guide pin 200. The tubular shaft 230 can pass over the guide pin 200 and engage the head 110 of the anchor 102. The anchor 102 can be pushed down the bone bore 84 to a desired depth. While applying downward pressure on the head 110 of the anchor 102 with the tubular shaft 230 toward the bone 80, the trigger 252 can be pulled upward away from the bone 80 pulling the guide pin 200. The guide pin 200 can exert a proximal force on the insert 120 to pull the intermediate portion 124 of the insert 120 into the body 102, urging the expanding members 106 outward and deploying the fixation device 100 in engagement with bone 80, as shown in FIGS. 8 and 9. Various other actuating arrangements for deploying the fixation device 100 can be used as described in the pending patent applications referenced above and incorporated herein by reference.

Referring to FIGS. 1, 3, 7, and 8, the fixation device 100 can include radial openings for delivering biologic material at the interface between the soft tissue 82 and the bone 80. In particular, radial delivery holes or other radial delivery apertures 114 can be formed around the circumference and through the body 104 of the anchor 102 at a distance "D" from the proximal surface of the head 110. The distance D is determined such that the delivery holes 114 are substantially at the level of the interface between the soft tissue 82 and the bone 80 when the fixation device is employed, as shown in FIG. 8. The delivery holes 114 can be aligned with and located proximally relative to the slots 116 of the expandable body 102. The insert 120 can also include openings 126, which can be aligned with the delivery holes 114 when the fixation device 100 is fully seated and deployed in engagement with the walls of the bone bore 84.

Figure 12:
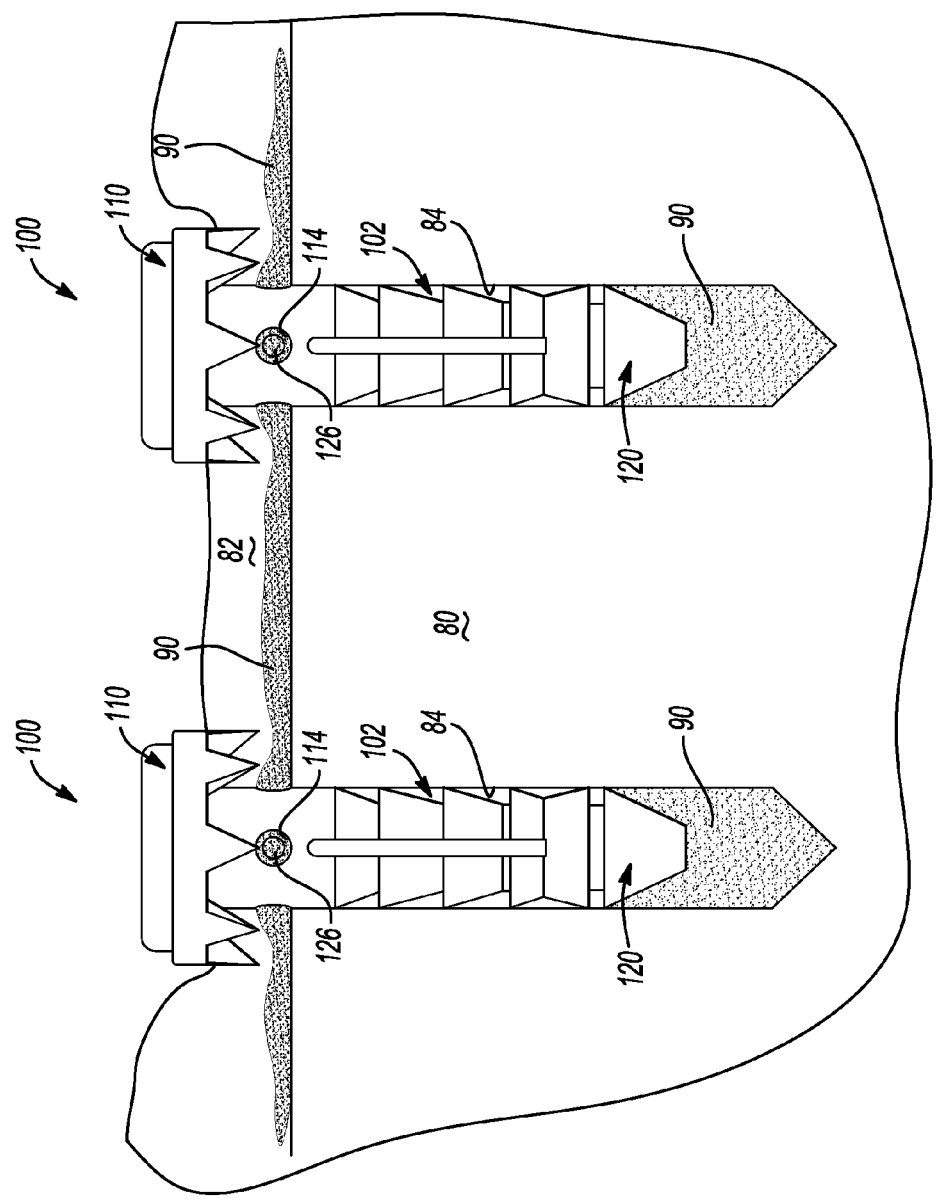
FIG. 12 is an environmental view of multiple fixation devices according to the present teachings showing delivery of biologic material through the fixation devices.

Referring to FIGS. 9-12, after the fixation device 100 is fully seated and deployed in engagement with the bone 80, the deployment instrument 250 together with the guide pin 200 can be decoupled from the tubular shaft 230 and removed leaving the tubular shaft 230 in engagement with the fixation device 100. Alternatively, the tubular shaft 230 can also be removed and replaced with a cannula that is positioned in communication with the longitudinal bore 118 along axis A of the fixation device 100. A syringe or other biologic delivery device 260 can be connected with the shaft 230 and used for delivering biologic material 90 through the longitudinal bore 236 of the tubular shaft 230 and the longitudinal bore 118 of the fixation device 100, as shown in FIG. 11. The biologic material can exit the aligned radial delivery holes 114, 126 of the anchor 102 and insert 120 and flow at the interface of the soft tissue 82 and bone 80. Optionally, biologic material 90 can also flow through the longitudinal bore 118 of fixation device 100 and fill the bone void at the bottom of the bone bore 84 in the bone 80, as also illustrated in FIG. 11, or not, as illustrated in FIG. 11A. It will appreciated than more than one fixation devices 100 can be used for securing the soft tissue 82 to the bone 80, as illustrated in FIG. 12, in which two fixation devices are shown.

It will be appreciated that the relative location of the delivery holes 114 of the body 104 and/or the delivery holes 126 of the insert 120 can be adjusted such that biologic material 90 can be delivered while the fixation device 100 is partially seated or partially deployed. In other aspects, seating or deploying the fixation device 100 can cause the delivery of biologic material 90, or delivering biologic material 90 can cause the fixation device 100 to be seated or deployed.

Figures 13A, 13B:
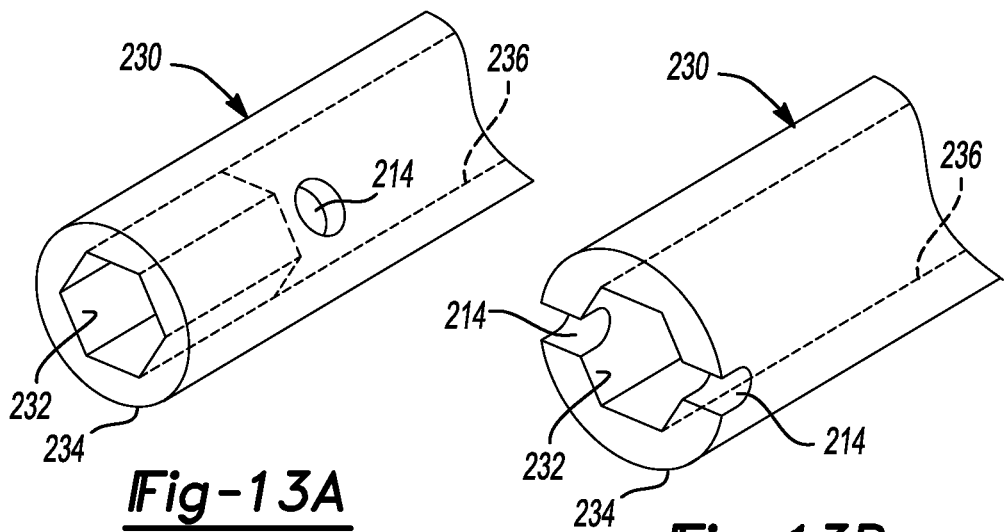
FIG. 13A is a detail of a delivery shaft that can be used with the fixation device of FIG. 13.
FIG. 13B is a detail of a delivery shaft that can be used with the fixation device of FIG. 13.

As discussed above, the present teachings are not limited to expandable fixation devices. Referring to FIGS. 13-13B, the present teachings are illustrated in connection with a fixation device 100 in the form of a threaded suture anchor that includes an eyelet 126 through which suturing or other flexible strands 218 can pass. The strands 218 can be attached to the soft tissue 82, thereby coupling the fixation device 100 to the soft tissue 82. A tubular shaft 230 can be used for inserting the fixation device 100 and for delivering the biologic material 90. The tubular shaft 230 can include one or more radial apertures 214 located along the shaft 230 and communicating with the longitudinal bore 236 of the tubular shaft 230 such that biologic material 90 can be delivered to the interface between the soft tissue 82 and the bone 80, while the fixation device 100 is partially or fully seated.

Referring to FIGS. 13A and 13B, the tubular shaft 230 can include an engagement surface 232, such as a hex surface, for engaging the proximal end of the fixation device 100 with an inserter or driver or other tubular delivery shaft 230. The radially located apertures 214 can be radial holes located off the distal end 234 of the tubular shaft 230, as shown in FIG. 13A, or slots located at the distal end 234 of the tubular shaft 230. The configuration of FIG. 13A can allow the delivery of biologic material 90 at the interface between the soft tissue 82 and the bone 80 before or after the fixation device 100 is fully seated, depending on the location of the radial apertures 214. The configuration of FIG. 13B can allow the delivery of biologic material 90 at the interface between the soft tissue 82 and the bone 80 before the fixation device 100 is fully seated.

As described above, the present teachings provide fixation devices 100 that can be used for delivering biologic material 90 at the interface of soft tissue 82 and bone 80. The fixation devices 100 can be, for example, rivets, expandable anchors, suture anchors, screws, or other devices that can be axially inserted in a pre-drilled bore in the bone 80 or threadably inserted directly into the bone 80. Biologic material 90 can be delivered at the interface of the soft tissue 80 and the bone 80 while the fixation device 100 is deployed, or when it is fully deployed or fully seated, or when it is partially deployed or partially seated. The biologic material 90 can be delivered through radial delivery apertures 114 of the fixation device 100 and/or through radial delivery apertures 214 of a cannulated insert 120 or an inserter or other tubular delivery shaft 230 that can be used for deploying, inserting or engaging the fixation device 100.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A fixation device for delivery of biologic material between soft tissue and a bone, the fixation device comprising:
  a cannulated anchor having a soft-tissue engaging portion and a bone-anchoring portion, the bone-anchoring portion including an expandable body having a proximal end and a distal end, the proximal end defining at least one radial delivery hole adjacent the soft-tissue engaging portion; and
  a cannulated insert engageable with the cannulated anchor, the insert having a proximal end and a distal end and defining at least one radial delivery hole at the proximal end of the insert, wherein the delivery holes of the anchor and insert are aligned and positioned such that the biologic material can be delivered through the delivery holes and flow between the soft tissue and an outer surface of the bone when the fixation device is deployed.

2. The fixation device of claim 1, wherein each of the anchor and insert further comprise a plurality of radial delivery holes positioned at the proximal end of the insert, and the delivery holes of the anchor are aligned with the delivery holes of the insert.

3. The fixation device of claim 1, wherein the anchor includes an enlarged annular head having a barbed surface for engaging soft tissue.

4. The fixation device of claim 1, wherein the expandable body includes a plurality longitudinal slots defining expandable members.

5. The fixation device of claim 4, wherein the radial delivery holes of the anchor are aligned with the longitudinal slots.

6. The fixation device of claim 1, wherein the cannulated insert includes a middle portion tapering proximally, a distal portion tapering distally, and a proximal portion.

7. The fixation device of claim 6, wherein the proximal portion includes a grip area for engaging an inner bore of the anchor.

8. The fixation device of claim 6, wherein the insert includes a pair of opposing flanges tapering proximally.

9. The fixation device of claim 1, further comprising a guide pin passing through the anchor and the insert, the guide pin operable for deploying the expandable body to an expanded configuration when the insert is fully seated within the anchor.

10. The fixation device of claim 9, in combination with a deployment instrument having a tubular shaft engageable with a head of the anchor.

11. The fixation device of claim 10, wherein the deployment instrument includes a trigger actuatably coupled to the guide pin.

12. A fixation device for delivery of biologic material between soft tissue and a bone, the fixation device comprising:
   an anchor having a first portion engaging the soft tissue and an expandable second portion adjacent the first portion and received in the bone below the soft tissue, the first portion having first and second ends, and the second portion having first and second ends, wherein the second end of first portion is adjacent the first end of the second portion; and
   an insert engageable with the anchor and received in the bone, wherein the anchor and insert are movable between a non-deployed and a deployed position, the fixation device defining a plurality of radial delivery holes positioned adjacent the first end of the second portion at an area between the soft tissue and the bone when the fixation device is in the deployed position, such that biologic material can be delivered through the delivery holes between the soft tissue and an outer surface of the bone.

13. The fixation device of claim 12, wherein the portion piercing soft tissue is an annular washer having a plurality of tissue-piercing formations.

14. The fixation device of claim 13, wherein the expandable portion includes a plurality of longitudinal slots defining expandable members.

15. The fixation device of claim 14, wherein the longitudinal slots are aligned with the delivery holes.

16. A fixation device for delivery of biologic material between soft tissue and a bone, the fixation device comprising:
   a cannulated anchor, the anchor having a head engageable with the soft tissue and an expandable body receivable in the bone, the anchor defining at least one radial delivery hole at a proximal portion of the anchor under the head; and
   a cannulated insert movable relative to the anchor for expanding the expandable body, the insert defining at least one radial delivery hole, wherein the delivery holes of the anchor and insert are aligned such that biologic material can be delivered through the delivery holes and flow between the soft tissue and an outer surface of the bone when the fixation device is deployed.

17. The fixation device of claim 16, further comprising a guide pin passing through the anchor and the insert, the guide pin operable for deploying the expandable body to an expanded configuration when the insert is fully seated within the anchor.

18. The fixation device of claim 17, in combination with a deployment instrument having a tubular shaft engageable with a head of the anchor.

19. The fixation device of claim 18, wherein the deployment instrument includes a trigger actuatably coupled to the guide pin.

20. The fixation device of claim 18, wherein the tubular shaft can be decoupled from the deployment instrument, the fixation device further comprising a syringe that is engageable to the shaft for delivery of the biologic material.

21. A fixation device for delivery of biologic material between soft tissue and a bone, the fixation device comprising: an anchor having a soft-tissue engaging portion and a bone-anchoring portion, the bone-anchoring portion including a body having a proximal end and a distal end, the proximal end of the bone anchoring portion defining at least one radial delivery aperture defined adjacent the soft-tissue engaging portion and adapted for delivering the biologic material through the anchor, wherein the anchor is expandable, the fixation device further comprising an expansion insert, the expansion insert defining at least one delivery aperture for delivering biologic material through the anchor and between the soft tissue and the bone.

22. The fixation device of claim 21, wherein the delivery aperture is positioned such that the biologic material can be delivered between the soft tissue and the bone when the anchor is fully seated.

23. The fixation device of claim 21, wherein the delivery aperture is positioned such that the biologic material can be delivered between the soft tissue and the bone when the anchor is partially seated.

24. A fixation device for delivery of biologic material between soft tissue and a bone, the fixation device comprising:
   an anchor extending from a first proximal end to a first distal end and defining a first longitudinal bore therethrough, the anchor having a body at the first proximal end and a plurality of expanding members at the first distal end, the body defining a first plurality of radially extending delivery bores in communication with the first longitudinal bore;
   an insert extending from a second proximal end to a second distal end and defining a second longitudinal bore therethrough, the insert defining a second plurality of radially extending delivery bores in communication with the second longitudinal bore, the insert configured to be positioned concentrically within the first longitudinal bore, where the first and second plurality of radially extending delivery bores can be radially aligned; and
   a head positioned at the proximal end of the body and having a plurality of anchoring protrusions for engaging the soft tissue, wherein upon aligning the first and second plurality of radially extending delivery bores and engaging the soft tissue with the plurality of anchoring protrusions, the first and second plurality of radially extending delivery bores is positioned a distance from the head and configured to deliver the biologic material between the soft tissue and an outer surface of the bone.

* * * * *

UNITED STATES PATENT AND TRADEMARK OFFICE
CERTIFICATE OF CORRECTION

PATENT NO.       : 8,574,275 B2                                     Page 1 of 1
APPLICATION NO.  : 12/881829
DATED            : November 5, 2013
INVENTOR(S)      : Kevin T. Stone et al.

It is certified that error appears in the above-identified patent and that said Letters Patent is hereby corrected as shown below:

In the Specification

Column 1, Line 9 After "11/745,226", insert --,--.

Column 2, Line 54 After "FIG. 1", insert --;--.

Column 4, Line 45 Delete "128a" and insert --118a--.

Column 4, Line 53 Delete "250," and insert --254,--.

Column 4, Line 64 Delete "102," and insert --104,--.

Column 5, Line 15 Delete "102." and insert --104.--.

Column 6, Line 20 Delete "80" and insert --82--.

Signed and Sealed this
Twenty-sixth Day of August, 2014

Michelle K. Lee
*Deputy Director of the United States Patent and Trademark Office*